United States Patent [19]

Nussbaum

[11] Patent Number: 5,352,207
[45] Date of Patent: Oct. 4, 1994

[54] VENTRICULAR DRAINAGE CATHETER WITH GUARD

[76] Inventor: Eric S. Nussbaum, 11712 Auth La., Silver Spring, Md. 20902

[21] Appl. No.: 885,129

[22] Filed: May 18, 1992

[51] Int. Cl.⁵ .............................................. A61M 5/32
[52] U.S. Cl. .................... 604/175; 128/748; 604/278
[58] Field of Search ........ 604/278, 264, 265, 174–180, 604/117; 128/748; 623/11

[56] References Cited

U.S. PATENT DOCUMENTS

| 4,307,719 | 12/1981 | McParland | 604/264 |
|---|---|---|---|
| 4,343,307 | 8/1982 | Reda | 604/278 |
| 4,623,348 | 11/1986 | Feit | 604/175 |
| 4,645,504 | 2/1987 | Byers | 604/175 |
| 4,676,782 | 6/1987 | Yamamoto et al. | 604/175 |
| 4,903,707 | 2/1990 | Knute et al. | 604/175 |
| 4,940,458 | 7/1990 | Cohn | 604/117 |
| 4,959,055 | 9/1990 | Hillyer | 604/278 |
| 5,061,281 | 10/1991 | Mares et al. | 623/11 |
| 5,085,646 | 2/1992 | Svenson et al. | 604/175 |
| 5,195,964 | 3/1993 | Kletzky et al. | 604/278 |

Primary Examiner—C. Fred Rosenbaum
Assistant Examiner—Chalin Smith
Attorney, Agent, or Firm—Sandler, Greenblum & Bernstein

[57] ABSTRACT

A method and apparatus for temporary, external, cerebral ventricular drainage in the treatment of hydrocephalus and intracranial hypertension are disclosed in which a flexible catheter having a repositionable guard surrounding its outer circumference with frictional gripping contact is inserted into the cerebral ventricle through a hole drilled in the skull. The guard is then advanced along the outside circumference of the catheter into a position, preferably the junction of the catheter and the skull hole, where the guard fixes the catheter in place and occludes the tract around the catheter by acting as a mechanical blockade and by encouraging a tissue fibrotic seal around the catheter. When the catheter is removed, the guard may be left in place inside the skull hole to eliminate any skull defect and to prevent the leakage of cerebrospinal fluid.

20 Claims, 6 Drawing Sheets

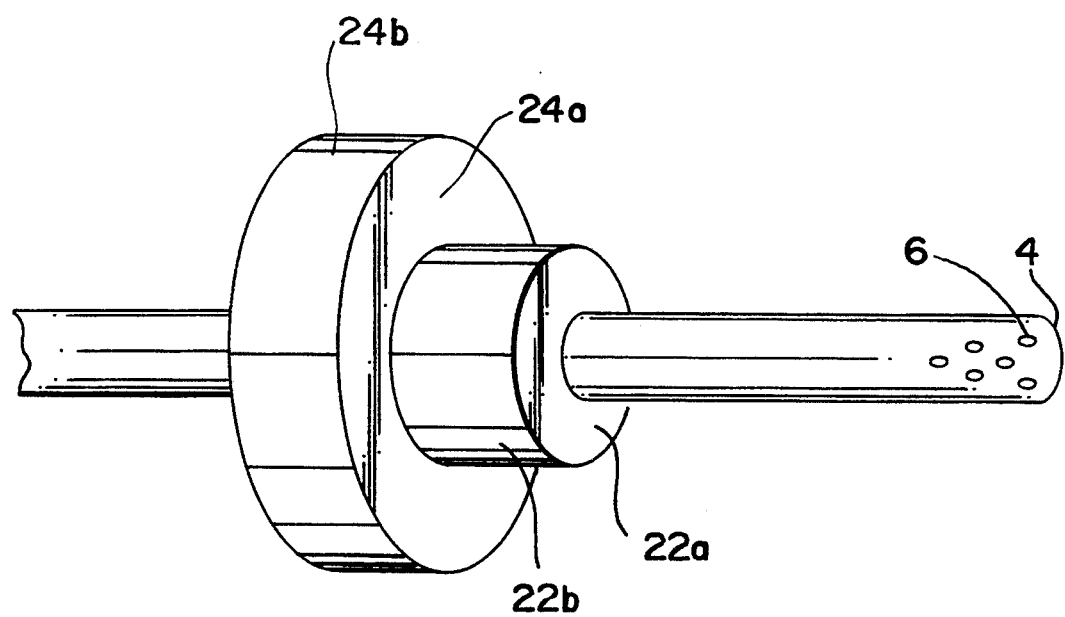
Fig_ 3

VENTRICULAR DRAINAGE CATHETER WITH GUARD

FIELD OF INVENTION

This invention relates to the art of neurological surgery, and in particular to an improved method and apparatus for the temporary, external drainage of cerebrospinal fluid from the cerebral ventricles.

DISCUSSION OF BACKGROUND INFORMATION

Temporary, external ventricular drainage (ventriculostomy) catheters are utilized in the treatment of hydrocephalus and intracranial hypertension, when the use of a permanent internal shunting system is not indicated i.e. when the problem is expected to resolve. The catheter is inserted via an incision made in the scalp skin and through a hole drilled in the underlying skull bone. The catheter is passed through the brain substance and into the ventricles which are the chambers deep within the brain that contain the cerebrospinal fluid (CSF).

The catheter allows for the monitoring of the intracranial pressure and also for the drainage of CSF, as necessary, to lower the intracranial pressure.

The use of a rubber catheter inserted percutaneously into the cerebral ventricles for the drainage of unwanted CSF was first described in 1943. (Crawford AS, Munslow RA: *Annals of Surgery* 117:798-799, 1943) Since that time, one of the major persisting risks associated with percutaneous ventricular drainage catheters has been infection of the brain or CSF. The catheter provides an open pathway for the migration of bacteria along the catheter and into the brain. A resulting infection (meningitis or ventriculitis), which has been reported to occur in up to 27% of patients with ventricular drainage catheters in place, may be life-threatening. (Mayhall CG, et al: *New England Journal of Medicine* 310:553-559, 1984) Because of this, many avenues have been explored to reduce the risk of ventricular drain infections.

Some neurosurgeons administer prophylactic antibiotics at the time of insertion of a ventricular drainage catheter and for as long as it remains in place. Nevertheless, the only study demonstrating a relative reduction in the rate of infection with the use of prophylactic antibiotics still reported an unacceptably high rate of infection (9%) in patients with ventricular drainage catheters. (Wyler AR, Kelly WA: *Journal of Neurosurgery* 37:185-187, 1972) Furthermore, many authorities suggest that this practice results in the selection of more virulent organisms that are resistant to the usual antibiotic agents thereby making any infection that does occur more dangerous and more difficult to treat. The routine use of prophylactic antibiotics for ventricular drainage catheters therefore remains controversial. (Stenager E, et al: *Acta Neurochirurgica* 83:20-23, 1986)

In many institutions, protocols have been established requiring that ventriculostomy catheters be changed to a new site every five to seven days, in an attempt to reduce infection by bacteria that colonize the catheter and migrate along its outer surface into the brain. (Mayhall CG, et al: *New England Journal of Medicine* 310:553-559, 1984) This requires a new scalp incision, a new hole drilled in the skull, and the passage of another catheter through the brain substance. This practice has not been clearly proven to reduce infection rates, and it also carries other risks, especially for those patients requiring external ventricular drainage for several weeks who may undergo four or five ventriculostomy changes. (Kanter RK, Weiner LB: *New England Journal of Medicine* 311:987, 1984) Each time a new catheter is placed, there is a new risk of injuring brain tissue and of causing dangerous bleeding by disrupting an artery or vein. Additionally, there is a new chance of introducing infection into the brain with each new passage of a foreign body.

Ideally, all ventricular drainage catheters are inserted under strict, sterile conditions such as in an operating room or in an intensive care unit setting. But in emergency situations, the catheter may have to be inserted under suboptimal conditions, for example in an emergency room. No matter how much precaution is exercised, the end result is still a percutaneous catheter that establishes a connection between an unsterile outside environment and the brain. This is simply an invitation for infection, and further measures to limit such infections are clearly necessary.

All temporary, external ventricular drainage catheter systems currently in use suffer from a number of disadvantages:

(a) The catheters pose a serious risk of infection to the brain and cerebrospinal fluid as bacteria can migrate along the open tract, around the catheters, as detailed above;

(b) The catheters are routinely changed approximately every five days which increases the chance of injuring the brain tissue or cerebral blood vessels, especially for patients who may require ventricular drainage for prolonged periods of time and thus require multiple catheter changes;

(c) The catheter is free at its entrance to the skull and may thus migrate inward, possibly injuring underlying brain tissue, or outward, possibly requiring its replacement and further increasing the risk of infection or injury;

(d) There is a free open space in the skull hole around the catheter and thus CSF may leak out around the catheter, invalidating measurements of intracranial pressure, and establishing a direct stream of CSF which connects the cerebral ventricles with the unsterile scalp and provides a patent conduit for migration of bacteria;

(e) A chronic leakage of CSF may develop after the catheter is removed, possibly necessitating further repair measures, as the hole drilled in the skull is left unsealed;

(f) A skull defect is left by the open drill hole once the catheter is removed.

SUMMARY OF THE INVENTION

Accordingly, several objects and advantages of the present invention are:

(a) To reduce the risk of infection associated with indwelling ventricular drainage catheters by establishing a physical barrier to the migration of bacteria along the catheter;

(b) To eliminate the need for, and accompanying risks of, routine changes of ventricular drainage catheters;

(c) To prevent the inward or outward migration of the catheter once in place by securing it as it dives through the hole in the skull;

(d) To diminish the risk of CSF leakage around the catheter by occluding the free space around the catheter in the skull hole, thereby improving the accuracy of intracranial pressure measurements and further decreasing the risk of cerebral infection;

(e) To diminish the risk of chronic leakage of CSF after the catheter is removed, by plugging the skull hole which is otherwise left open after catheter removal;

(f) To eliminate the skull defect which remains after the catheter is removed by plugging the skull hole.

Still further objects and advantages will become apparent from a consideration of the ensuing descriptions and drawings.

BRIEF DESCRIPTION OF THE DRAWINGS

FIG. 3 shows a close-up view of a guard on a ventricular catheter.

Reference Numerals in Drawings

1—ventricular catheter
2—cerebral ventricle filled with CSF
4—ventricular end of catheter
6—perforations in catheter
8—brain cortical surface
10—dura mater
14—outside surface of skull bone
16—skull bone
18—skull hole
20—guard
22—disc of smaller diameter
22a—anterior face of disc of smaller diameter
22b—lateral surface of disc of smaller diameter
24—disc of larger diameter
24a—anterior face of disc of larger diameter
24b—lateral surface of disc of larger diameter
26—skin incision site for drill hole
28—skin exit site for ventricular drainage catheter
30—scalp skin
32—external end of ventricular catheter
34—connector device
36—connection tubing
38—collection bag
40—stylet
42—trocar

DETAILED DESCRIPTION OF THE PREFERRED EMBODIMENTS

Figure 2A:
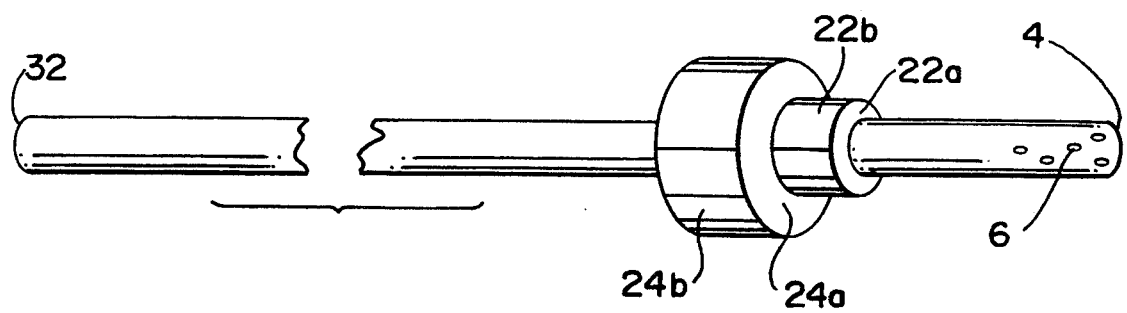
FIG. 2 shows a ventricular drainage catheter with guard before insertion, and a stylet and trocar.
Figure 2B:
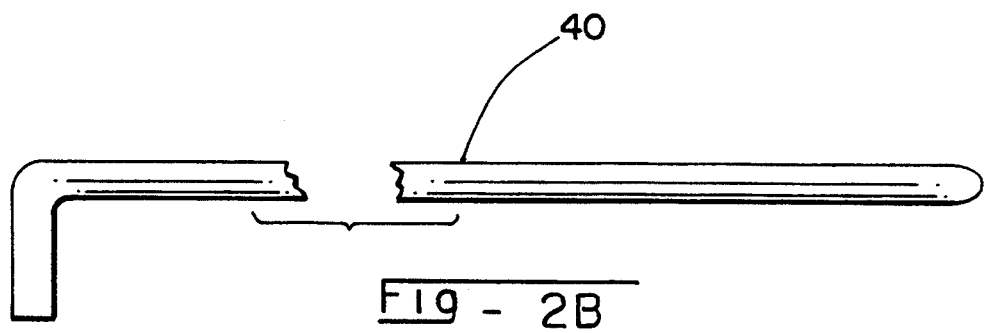
Figure 2C:
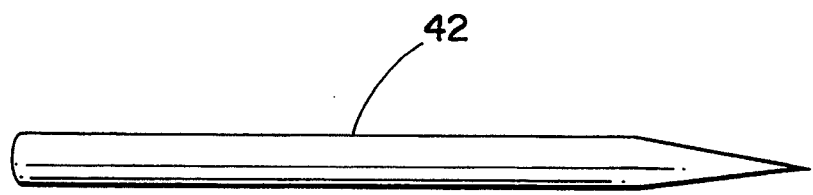

Referring now to the drawings in detail, FIG. 2 illustrates a catheter 1 which is made of a soft silicone rubber or of any other suitable, tissue-compatible material. The catheter has a rounded ventricular end 4 with multiple perforations 6 and an open external end 32. The following are exemplary measurements, which may be altered significantly without changing the efficacy of the catheter. Catheter 1 is approximately 34 centimeters in length from ventricular end 4 to external end 32, with an internal diameter of approximately 1.4 millimeters and an outer diameter of approximately 3.0 millimeters.

Approximately 12 centimeters from ventricular end 4 of catheter 1, is a repositionable guard 20 that snugly encircles the outside circumference of the catheter, and that may be slipped along the outside of the catheter with gentle traction. Guard 20 may be made of a number of tissue-ingrowth promoting substances such as woven felts, velours, textured polymers, collagens, or sponge-like materials. The surface of guard 20 may be textured and irregular, further promoting tissue ingrowth. The ingrowth of body tissue into the guard matrix forms a seal around the catheter. The guard matrix is initially in a relatively compressed form. As the matrix absorbs body fluids, the guard expands, further sealing the tract around the catheter.

A straight, steel stylet 40 and a steel trocar 42, which are used during the insertion of the catheter, are also shown. Stylet 40 should be approximately 2 centimeters longer than catheter 1 and should be of a diameter 0.25 centimeters smaller then the internal diameter of catheter 1 so that stylet 40 fits inside the lumen of catheter 1, to keep the catheter straight during insertion. Trocar 42 should have a needle-sharp tip and a dull end of diameter approximately equal to the internal diameter of catheter 1 so that trocar 42 securely fits inside the lumen of catheter 1 so that it can be temporarily attached to the open, external end 32 of catheter 1 and used to tunnel the catheter as described below.

FIG. 3 illustrates a close-up view of the preferred embodiment of guard 20 in which the guard is composed of two circular discs, 22 and 24, of different diameters, concentrically stacked on one another. The height of each disc is approximately 3 millimeters. The discs have diameters of approximately 5 millimeters and 1 centimeter, with the disc of smaller diameter resting on top of the disc of larger diameter. Each disc has a hole in its center of diameter just large enough to encircle the outer circumference of the catheter with frictional gripping contact, with the holes being exactly aligned when the discs are stacked. The disc of smaller diameter 22 projects forward from the anterior face 24a of the disc of larger diameter 24, leaving a circular, outer rim of the anterior face 24a of the disc of larger diameter 24 exposed.

Catheter 1 passes through the holes of the attached discs, and thus guard 20 encircles the outer circumference of catheter 1. Guard 20 is oriented with the disc of smaller diameter 22 being closer to ventricular end 4 of catheter 1, and the disc of larger diameter 24 closer to the external end 32 of catheter 1. Guard 20 may be repositioned to any location on catheter 1 by slipping the guard along the outside of the catheter with gentle traction.

Figure 4:
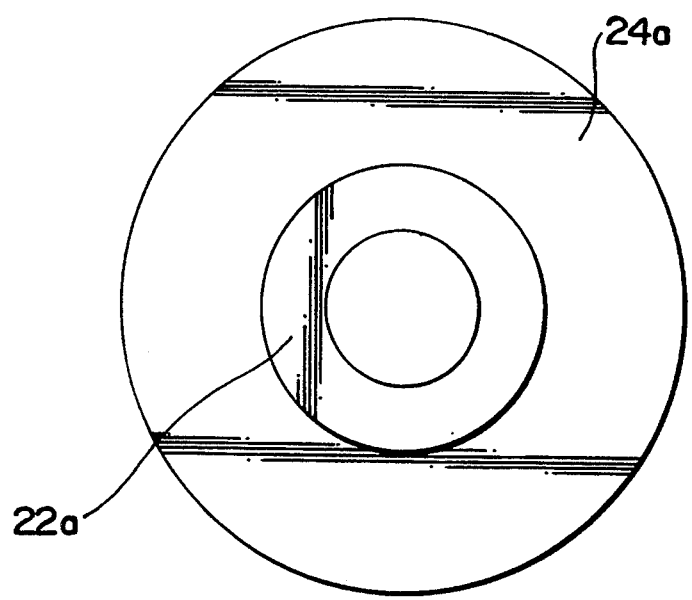
FIG. 4 shows an en-face view of a catheter guard.

In FIG. 4, an en-face view of guard 20 is shown. The disc of smaller diameter 22 is seen to project outwards from the anterior face 24a of the disc of larger diameter 24 leaving the outer rim of the anterior face 24a of the disc of larger diameter 24 exposed. It is this outer rim that contacts the outside surface 14 of skull bone 16 just surrounding skull hole 18 after the guard is slipped into position along catheter 1, as will be described below in FIG. 1, and in exploded view, in FIG. 5.

The particular two-tiered disc configuration shown in FIGS. 3 and 4 represents just one possible shape for the guard, as a single disc which is advanced into the hole, or a guard of another shape entirely may be substituted so long as the space around the catheter in the skull hole is effectively occluded.

Figure 1:
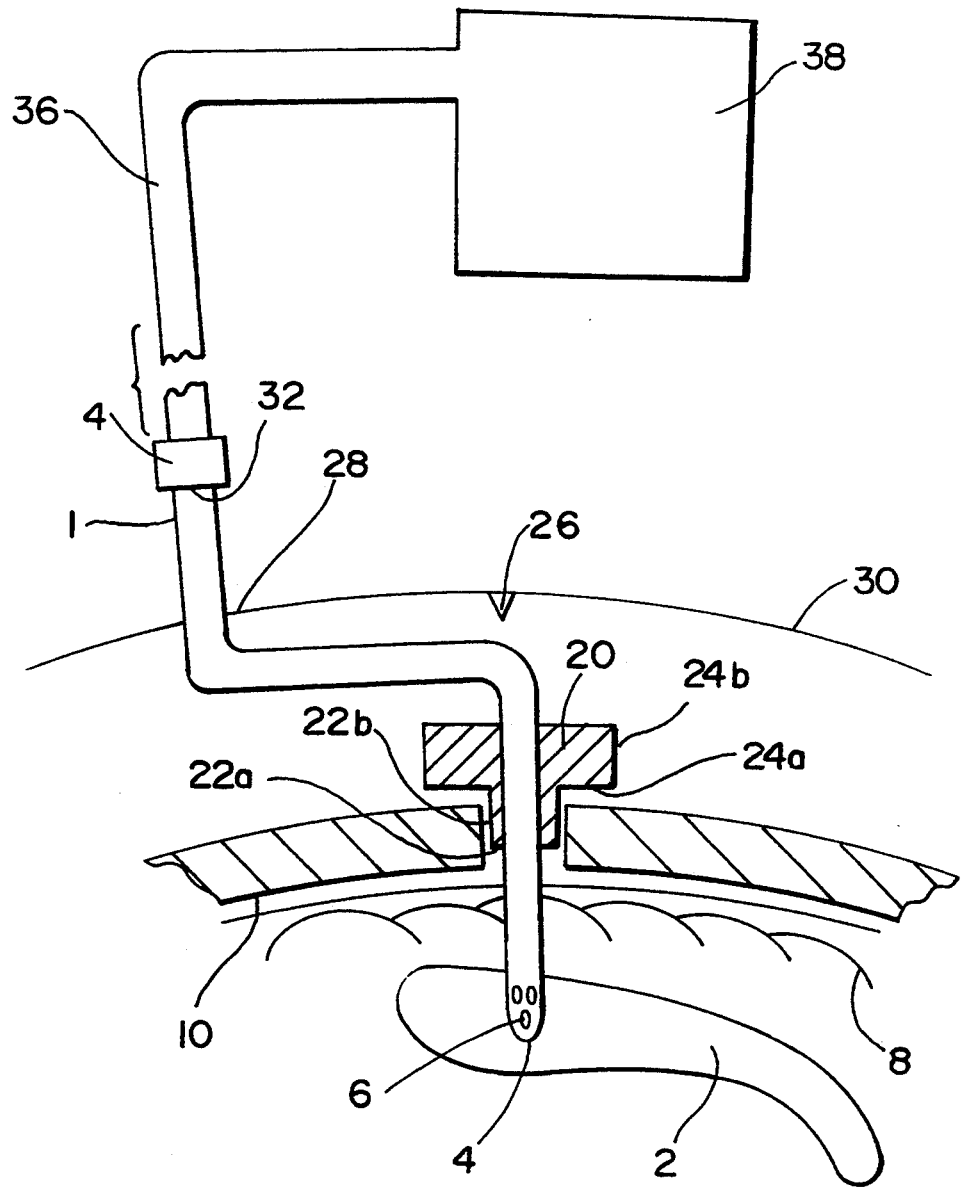
FIG. 1 shows a lateral view of an external, ventricular drainage catheter with guard, after insertion into a cerebral ventricle, draining ventricular fluid.

FIG. 1 illustrates catheter 1 with guard 20, after insertion into a cerebral ventricle 2. Ventricular end 4 of catheter 1 rests inside cerebral ventricle 2 which contains CSF. The CSF flows into the catheter lumen via the perforations 6 in catheter 1. The course of catheter 1 may be followed out of the ventricle, through brain tissue, to emerge from the brain cortical surface 8. The catheter passes through an opening in the dura mater 10, a firm membrane that covers the brain, and then out through a hole 18 which has been drilled in skull bone 16.

Guard 20 encircles catheter 1 and is positioned at the junction of catheter 1 and skull hole 18, occluding the space in the hole around the catheter. The catheter makes a curve of not quite 90 degrees after emerging from the skull hole, to travel in a subgaleal tunnel, gradually continuing upward through the galeal tissue, to emerge at a scalp skin 30 exit site 28 approximately 5 centimeters from a skin incision 26 overlying skull hole 18.

The catheter now travels outside of the body, and external end 32 of catheter 1 is attached, via a conventional plastic connecting device 34 to a drainage tubing 36 made of a suitable vinyl or plastic polymer. The tubing may be of variable length, but it should be long enough to prevent excessive traction on the catheter during routine nursing care. At least 3 feet of tubing is recommended. The tubing 36 runs to a collection bag 38, into which the CSF drips and collects at the bottom of the bag. The bag, like the tubing, may be made of a vinyl or a suitable plastic polymer, but should preferably be made of a transparent material, through which one can see and measure the volume of CSF in the bag. The bag may also be of variable size but a 1 liter bag is recommended.

Figure 5:
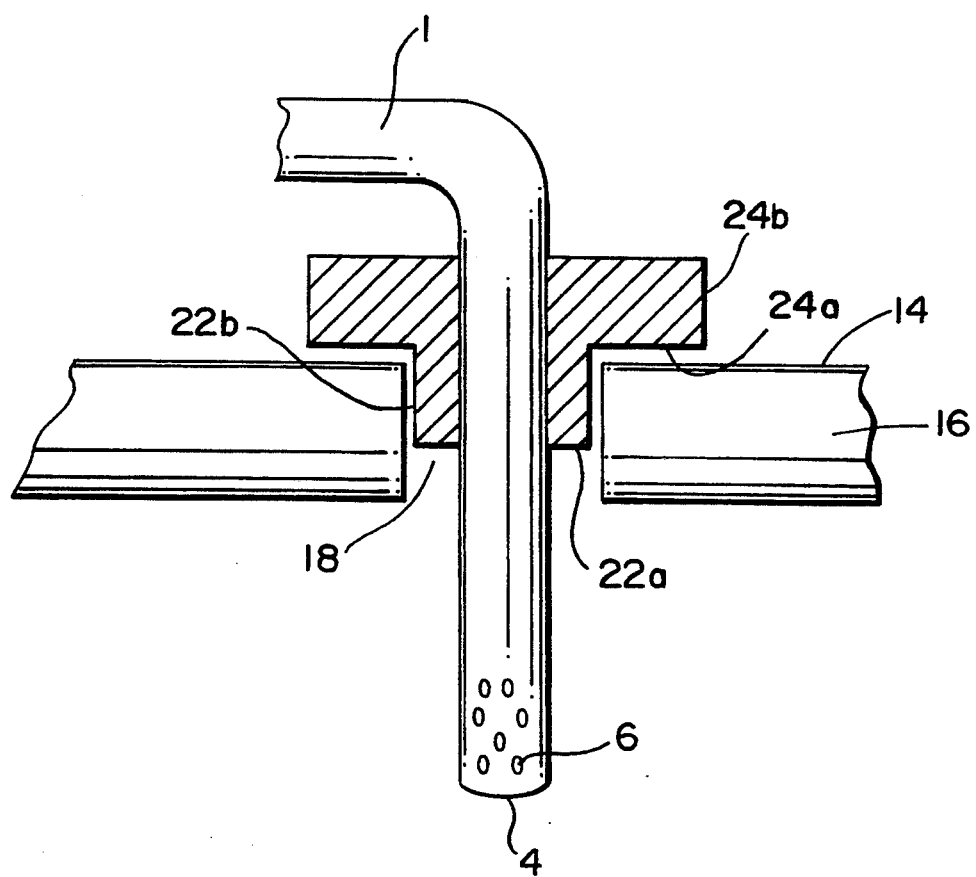
FIG. 5 shows an expanded side view of a guard on a ventricular catheter, positioned inside the skull hole.

In FIG. 5, guard 20 is illustrated in position in skull hole 18, reflecting the preferred embodiment of the invention. The disc of smaller diameter 22 is positioned inside skull hole 18, occluding the space around catheter 1. The lateral wall 22b of the disc of smaller diameter 22 is flush against the inner wall of skull hole 18. The outer rim of the anterior face 24a of the disc of larger diameter 24 is flush against the outside surface 14 of skull bone 16 surrounding skull hole 18, further preventing CSF leakage around catheter 1, and also promoting subgaleal tissue fibrosis around the catheter.

Figure 6:
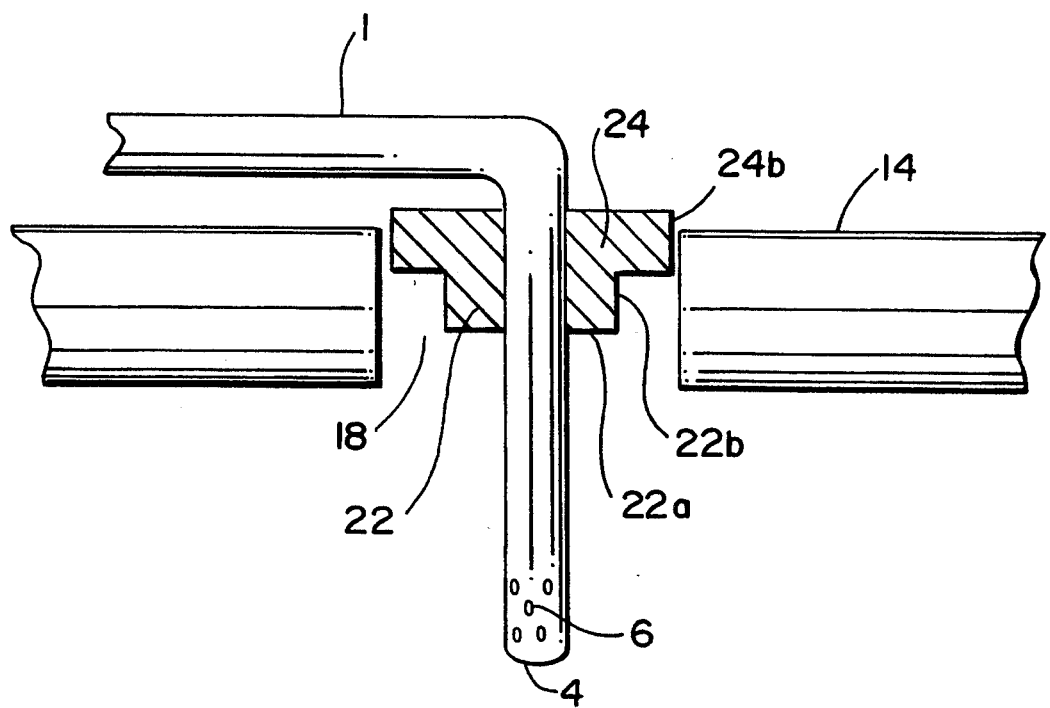
FIG. 6 shows an expanded side view of a guard on a ventricular catheter, positioned inside a larger skull hole.

FIG. 6 illustrates another embodiment, in which a hole of larger diameter has been drilled in the skull. In order to fully occlude this larger hole, both the disc of smaller diameter 22 and the disc of larger diameter 24 are advanced into the skull hole, so that the lateral wall 24b of the disc of larger diameter 24 is flush against the inner wall of the skull hole, occluding the space around the catheter.

Operation of Invention

The temporary, external ventricular drainage catheter with guard is inserted in a fashion similar to conventional, temporary, ventricular drainage catheters. Under sterile conditions, an area of the scalp is shaved, washed with an antiseptic solution, and then draped with sterile towels. An incision 26 is made in the scalp 30 (FIG. 1) in any number of locations which will provide a trajectory to the ventricle that does not traverse eloquent or vital brain tissue. One such site may be found by starting at the midline bridge of the nose, moving approximately 12 centimeters along a line straight back over the forehead, and then moving 3 centimeters laterally in either direction along a line perpendicular to the first line. Of course, the specific site chosen for insertion of the catheter will depend on the reason necessitating its implantation in any given patient.

The incision is continued down through the scalp or galeal tissue to skull bone 16. Next, a hole 18 is drilled in the skull, typically using a hand-held twist drill yielding a hole with a diameter of approximately 5 millimeters, although a larger drill bit or an electric drill may be used, yielding a hole with a slightly larger diameter.

The dura mater 10, which lies just beneath skull bone 16, is pierced with a needle or with a knife blade to allow for the passage of catheter 1. Stylet 40 is placed within the lumen of catheter 1 to allow for easier, more accurate passage of the catheter. (FIG. 2) Catheter 1 is then passed through scalp incision 26, through skull hole 18, through the dural opening, through the surface 8 and substance of the brain, and into the fluid-filled cerebral ventricle 2. Passing the catheter to a depth between six and eight centimeters will usually place the catheter in the ventricle, although some variability is expected. Stylet 40 is removed, and CSF should flow freely from external end 32 of catheter 1.

In the preferred embodiment, shown in FIGS. 1 and 5, guard 20 which encircles the outer circumference of catheter 1 and which is initially positioned 12 centimeters from ventricular end 4 of the catheter, is advanced along the catheter with gentle traction, until the anteriorly projecting, disc of smaller diameter 22 lies within skull hole 18, and the outer rim of the anterior face 24a of the disc of larger diameter 24 is flush with the portion of outside surface 14 of skull bone 16 that just surrounds skull hole 18. In the setting of a larger skull hole, as depicted in FIG. 6, the disc of larger diameter 24 may be advanced into the skull hole as well, so that the hole is plugged by the larger disc. The skull hole should be fully occluded by catheter 1 and surrounding guard 20 so that no CSF may leak around the catheter.

The guard matrix is initially in a relatively compressed state which allows for easy insertion into the skull hole. As the matrix absorbs body fluids, it expands and occludes the skull hole. Over several days, the body tissues grow into the guard matrix, causing a solid fibrosis that further seals the skull hole. This acts as a blockade to the inward migration of bacteria or the outward leakage of CSF around the catheter. It also fixes the catheter securely in place.

Trocar 42 is inserted into external end 32 of catheter 1, temporarily attaching the catheter to the trocar. Trocar 42 is then used to tunnel the catheter under and then up through the galeal tissue to emerge through the skin at a second site 28 approximately five centimeters from the original scalp incision 26. The catheter is typically secured at the skin site with a suture. The trocar is removed, and drainage tubing 36 is attached to external end 32 of catheter 1 via a conventional connecting device 34. The tubing runs to collection bag 40, into which the CSF drains. The height of the collection system determines the rate of CSF drainage.

When the ventricular catheter is no longer required for the drainage of CSF, it is removed by palpating the catheter and guard under the scalp skin where the catheter emerges from skull hole 18, and then applying firm pressure to the skin at this location to hold the guard in place, while applying traction to external end 32 of catheter 1 at skin exit site 28. The catheter is thereby removed, leaving guard 20 in place in skull hole 18. The skull defect is thus eliminated as the guard remains in the skull hole, and continues to encourage the ingrowth of natural fibrous tissue. The risk of chronic leakage of CSF is diminished as well, since the skull hole is occluded by guard 20, preventing the egress of fluid.

Accordingly, the reader will see that the external ventricular drainage catheter with guard can be used to establish drainage of unwanted CSF and to monitor intracranial pressure, while significantly reducing the risk of ventricular drain infection by occluding the otherwise open tract around the catheter. It thus provides an important improvement over the prior art and has the following additional advantages:

it obviates the need for, and risks of, routine ventricular drainage catheter changes;

it will not migrate inward, possibly injuring underlying brain tissue, or outward, possibly necessitating its replacement;

it diminishes the risk of CSF leakage around the catheter by occluding the open tract and the open space around the catheter in the skull hole, thereby improving the accuracy of intracranial pressure measurements and further decreasing the risk of cerebral infection;

it diminishes the risk of chronic CSF leakage after removal of the catheter by leaving the guard in the skull hole, thereby preventing the continued egress of CSF;

it eliminates the skull defect that typically remains after removal of the catheter by leaving the guard in the skull hole;

Although the description above contains many specifities, these should not be construed as limiting the scope of the invention but as merely providing illustrations of some of the presently preferred embodiments of this invention. Various modifications to the embodiments described above will be apparent to those skilled in the art. For example, the shape of the guard may be changed without altering its effectiveness, the outer surface of the guard may be impregnated with a substance having antibacterial properties, or the guard may be attached to a permanent internal CSF shunting system.

Thus the scope of the invention should be determined by the appended claims and their legal equivalents, rather than by the examples given.

I claim:

1. A neurosurgical apparatus for the drainage of cerebrospinal fluid from ventricles of the brain, comprising:

a flexible catheter, including an outer surface, suitable for surgical implantation in a patient through a skull hole drilled in a skull bone of the patient;

a repositionable guard comprising a larger portion, a smaller portion projecting from said larger portion, and an outer surface comprising a material that promotes ingrowth of body tissue;

each of said smaller portion and said larger portion including a hole capable of encircling said outer surface of said catheter with frictional gripping contact; and at least said smaller portion is positionable inside the skull hole, and said guard is positionable at a point of entry of said catheter to the skull hole so that a space around said catheter in the skull hole is substantially occluded.

2. The neurosurgical apparatus of claim 1, wherein said material that promotes ingrowth of body tissue is selected from the group consisting of velour, woven felt, sponge, foam and collagen.

3. The neurosurgical apparatus of claim 2, wherein said material that promotes ingrowth of body tissue is sponge.

4. The neurosurgical apparatus of claim 1, wherein said larger portion comprises an outer surface extending past said smaller portion, said outer surface being capable of contacting the outside surface of the skull bone surrounding said skull hole.

5. The neurosurgical apparatus of claim 1, wherein each of said larger portion and said smaller portion has a height of about 3 millimeters.

6. The neurosurgical apparatus of claim 1, wherein said material that promotes ingrowth of body tissue is textured.

7. The neurosurgical apparatus of claim 1, wherein said catheter includes a ventricular end, and said smaller portion is oriented toward said ventricular end.

8. The neurosurgical apparatus of claim 1, wherein said guard is at least partially constructed of a compressible material.

9. The neurosurgical apparatus of claim 1, wherein said smaller portion and said larger portion comprises one piece.

10. The neurosurgical apparatus of claim 1, wherein said smaller portion and said larger portion comprises separate elements.

11. The neurosurgical apparatus of claim 10, wherein said separate elements comprise two concentrically stacked discs, said smaller portion comprising a smaller diameter disc and said larger portion comprising a larger diameter disc.

12. The neurosurgical apparatus of claim 11, wherein said smaller diameter disc has a diameter of about 5 millimeters, and said larger diameter disc has diameter of about 1 centimeter.

13. The neurosurgical apparatus of claim 12, wherein each of said larger portion and said smaller portion has a height of about 3 millimeters.

14. The neurosurgical apparatus of claim 11, wherein said hole in each of said smaller diameter disc and said larger diameter disk is substantially centrally positioned.

15. The neurosurgical apparatus of claim 11, wherein said larger diameter disc includes an outer rim portion that extends past said smaller diameter disc, and said outer rim portion is capable of contacting the outside surface of the skull bone surrounding the skull hole, and said smaller diameter disc includes an edge portion capable of being positioned flush against the inner wall of the skull hole.

16. The neurosurgical apparatus of claim 15, wherein said material that promotes ingrowth of body tissue is selected from the group consisting of velour, woven felt, sponge, foam and collagen.

17. The neurosurgical apparatus of claim 1, wherein said larger portion comprises a lateral wall, and said lateral wall is capable of being positioned flush against the inner wall of the skull hole.

18. The neurosurgical apparatus of claim 1, wherein said larger portion includes an outer rim portion that extends past said smaller portion, and said outer rim portion is capable of contacting the outside surface of the skull bone surrounding the skull hole, and said smaller portion includes an edge portion capable of being positioned flush against the inner wall of the skull hole.

19. The neurosurgical apparatus of claim 1, wherein said hole in each of said smaller diameter disc and said larger diameter disk is substantially centrally positioned.

20. The neurosurgical apparatus of claim 9, wherein said hole in each of said smaller diameter disc and said larger diameter disk is substantially centrally positioned.

* * * * *